United States Patent [19]  [11] 4,019,892
Pilgram  [45] Apr. 26, 1977

[54] HERBICIDAL HETEROCYCLIC COMPOUNDS
[75] Inventor: Kurt H. G. Pilgram, Modesto, Calif.
[73] Assignee: Shell Oil Company, Houston, Tex.
[22] Filed: Dec. 31, 1975
[21] Appl. No.: 645,598
[52] U.S. Cl. .................................. 71/88; 260/340.2
[51] Int. Cl.² ........................................ C07D 317/34
[58] Field of Search ...................... 260/340.2; 71/88
[56] References Cited
UNITED STATES PATENTS 3,183,074  5/1965  Walworth et al. ...................... 71/88
3,644,422  2/1972  Mine et al. ............................. 71/88
3,877,921  4/1975  Timmons et al. ....................... 71/88

FOREIGN PATENTS OR APPLICATIONS 256,106    8/1967  Austria ........................... 260/340.2
1,263,779  3/1968  Germany ......................... 260/340.2
1,059,710  6/1959  Germany ............................... 71/88

Primary Examiner—Norma S. Milestone

[57] ABSTRACT

Compounds of the formula

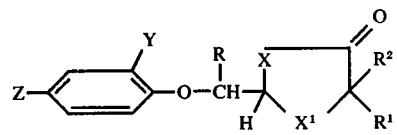

wherein X is O or $NR^3$ in which $R^3$ is hydrogen or alkyl; $X^1$ is oxygen or sulfur; Y is hydrogen, halogen, cyano, alkyl, alkoxy, haloalkoxy, alkylthio or haloalkyl; Z is hydrogen, halogen, alkyl, alkoxy or haloalkyl; and $R^1$ and $R^2$ each independently may be hydrogen, alkyl, aryl or aralkyl and R is hydrogen or methyl are useful as herbicides.

9 Claims, No Drawings

HERBICIDAL HETEROCYCLIC COMPOUNDS

BACKGROUND OF THE INVENTION

1. Field of the Invention

This invention relates to new heterocyclic compounds, their use as herbicides and to herbicidal compositions containing these new heterocyclic compounds.

2. Summary of the Invention

The present invention is directed to new heterocyclic compounds of formula I below:

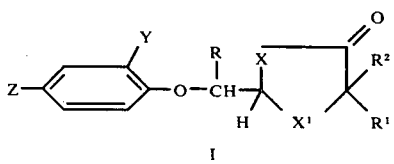

I wherein X is O or $NR^3$ in which $R^3$ is hydrogen or alkyl; $X^1$ is oxygen or sulfur; Y is hydrogen, halogen, cyano, alkyl, alkoxy, haloalkoxy, alkylthio or haloalkyl; Z is hydrogen, halogen, alkyl, alkoxy, haloalkoxy or haloalkyl; $R^1$ and $R^2$ each independently is hydrogen, alkyl, aryl or aralkyl and R is hydrogen or methyl.

Typical compounds of this invention are those of formula I above wherein Y is hydrogen, halogen of atomic number 9–35, inclusive, that is fluorine, chlorine or bromine, cyano, alkyl, alkoxy or alkylthio of 1 to 6 carbon atoms each optionally substituted by one or more halogen of atomic number 9–35, inclusive; Z is hydrogen, halogen, preferably chlorine or bromine, alkyl or alkoxy of 1–6 carbon atoms optionally substituted by halogen; $R^1$ and $R^2$ each independently is hydrogen, alkyl of 1 to 6 carbon atoms or aryl or aralkyl of up to 8 carbon atoms, such as phenyl, benzyl or phenethyl; and $R^3$ is hydrogen or alkyl of 1 to 6 carbon atoms and R is hydrogen or methyl, preferably hydrogen.

Typical compounds contemplated for use within the scope of this invention include:

2-phenoxymethyl-1,3-dioxolan-4-one
2-(2,4-dibromophenoxymethyl)-1,3-dioxolan-4-one
2-(2-(trifluoromethyl)-4-fluorophenoxymethyl)-1,3-dioxolan-4-one
2-(2,4-dimethylphenoxymethyl)-1,3-dioxolan-4-one
2-(2,4-difluorophenoxymethyl)-1,3-oxathiolan-5-one
2-(4-chlorophenoxymethyl)-4,4-diphenyl-1,3-oxathiolan-5-one
2-(2-methoxy-4-bromophenoxymethyl)-5-methyl-1,3-dioxolan-4-one
2-(2,4-di(trifluoromethyl)phenoxymethyl)-1,3-oxathiolan-5-one
2-(2-(trifluoromethyl)-4-fluorophenoxymethyl)-1,3-oxathiolan-5-one
2-phenoxymethyl-1,3-oxathiolan-5-one
2-(2,4-dimethylphenoxymethyl)-1,3-oxathiolan-5-one
2-(2-fluoro-4-methylphenoxymethyl)-1,3-dioxolan-4-one
2-(4-trifluoromethoxyphenoxymethyl)-1,3-dioxolan-4-one
2-(2-methoxy-4-methylophenoxymethyl)-1,3-dioxolan-4-one
2-(α-methyl-phenoxymethyl)-1,3-dioxolan-4-one
2-(alpha-methyl-phenoxymethyl)-1,3-oxathiolan-5-one
2-(4-methylphenoxymethyl)-4-phenyl-1,3-oxathiolan-5-one
2-(4-bromophenoxymethyl)-4,4-dimethyl-1,3-oxathiolan-5-one
2-phenoxymethyl-1,3-oxazolidin-4-one
2-(2,4-dibromophenoxymethyl)-5-methyl-1,3-oxazolidin-4-one
2-(4-methylphenoxymethyl)-5-phenyl-1,3-oxazolidin-4-one
2-(2-trifluoromethyl-4-fluorophenoxymethyl)-1,3-oxazolidin-4-one
2-(4-methoxy-2-chlorophenoxymethyl)-1,3-oxazolidin-4-one
2-(2-fluoro-4-chlorophenoxymethyl)-1,3-oxazolidin-4-one
2-(2-chloro-4-bromophenoxymethyl)-3,5-dimethyl-1,3-oxazolidin-4-one
2-(2,4-difluorophenoxymethyl)-1,3-thiazolidin-4-one
2-(4-methyl-2-bromophenoxymethyl)-3,5-dimethyl-1,3-thiazolidin-4-one
2-(2-trichloromethyl-4-chlorophenoxymethyl)-1,3-thiazolidin-4-one
2-(4-ethoxy-2-chlorophenoxymethyl)-5-phenyl-1,3-thiazolidin-4-one
2-(2-bromo-4-chlorophenoxymethyl)-1,3-thiazolidin-4-one
2-(2-chloro-4-fluorophenoxymethyl)-1,3-thiazolidin-4-one Preferred because of their herbicidal properties are those compounds of formula I wherein Y is halogen, preferably chlorine, or alkyl, preferably methyl; Z is halogen, preferably chlorine; $R^1$ is hydrogen or alkyl, preferably methyl, $R^2$ is hydrogen and R is hydrogen. For Example:

2-(2-methyl-4-chlorophenoxymethyl)-1,3-oxazolidin-4-one
2-(2-methyl-4-chlorophenoxymethyl)-3-methyl-1,3-oxazolidin-4-one
2-(2-methyl-4-chlorophenoxymethyl)-3,5-dimethyl-1,3-oxazolidin-4-one
2-(2-methyl-4-chlorophenoxymethyl)-5,5-dimethyl-1,3-dioxolan-4-one
2-(2-methyl-4-chlorophenoxymethyl)-1,3-dioxolan-4-one Expecially active are those species wherein Y and Z are halogen, preferably chlorine and R, $R^1$ and $R^2$ are each hydrogen. For example: 2-(2,4-dichlorophenoxymethyl)-1,3-dioxolan-4-one and 2-(2,4-dichlorophenoxymethyl)-1,3-oxathiolan-5-one.

In general the dioxolanes (X=O, $X^1$=O) are somewhat more active than the oxathiolanones (X=O, $X^1$=S), oxazolidinones (X=$NR^3$, $X^1$=O) or the thiazolidinones (X=$NR^4$, $X^1$=S).

It will be appreciated that when $R^1 \neq R^2$ that the heterocyclic compounds of the invention may exhibit geometrical isomerism. The individual isomers together with mixtures thereof are included within the scope of the invention. It will also be appreciated that certain isomers of the heterocyclic compounds of the invention have more activity than the other isomers and that it may be desirable to effect separation of the more active component.

The heterocyclic compounds of the present invention are readily prepared by synthesis methods known in the art.

The preferred method for obtaining the heterocyclic compounds of the present invention involves the condensation of a carbonyl compound with an α-hydroxy carboxylic acid or amide thereof. Thus the specific carbonyl reactant used is the appropriate substituted phenoxyacetaldehyde, such as (4-chlorophenoxy)-, (2,4-dichlorophenoxy)-, or (2-chloro-4-methylphenoxy)acetaldehyde. The α-hydroxy acid to be used includes the following: glycolic, thioglycolic, lactic, α-hydroxy-dimethylacetic or mandelic acid or an amide thereof.

Acidic catalysts are used in the condensation reaction, for example: benzene- or p-toluenesulfonic acid and activated Montmorillonite. However, I prefer to use the Lewis acid, boron trifluoride in the form of the etherate, $BF_3$—$O(C_2H_5)_2$, which permits the condensation to be carried out successfully at ambient temperature without azeotropic removal of water. The reaction is conducted in the presence of a solvent. Suitable solvents include ethyl ether and tetrahydrofuran. Reaction products may be purified using conventional techniques. Geometric isomers are readily separated by silica chromatography.

As mentioned above the heterocyclic compounds are of interest as herbicides, preferably for pre-emergence application. The invention includes, therefore, herbicidal compositions comprising a carrier and/or a surface active agent, together with, as active ingredient, a heterocyclic compound of the invention. Likewise the invention also includes a method of combating weeds at a locus which comprises applying to the locus a heterocyclic compound or composition of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the composition of the invention, and suitable examples of these are to be found, for example, in UK patent specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75% w of toxicant and usually contain, in addition to solid carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilizers, slow release modifiers and binding agents. Emulsifiable concentrates usually contain, in addition to the solvent and, when necessary, co-solvent, 10–50% w/v active ingredient, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w active ingredient, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the active ingredient is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, especially insecticidal, acaricidal, herbicidal or fungicidal properties.

EXAMPLES

The preparation and properties of the compounds of the invention are illustrated by the following examples. It should be understood, however, that the examples given are for the purpose of illustration only and are not to be regarded as limiting the invention in any way. In the examples below, the structure of all the products prepared was confirmed by elemental, nuclear magnetic resonance and infrared analyses.

EXAMPLE 1

2-(4-chlorophenoxymethyl)-5-methyl-1,3-dioxolan-4one, cis and trans isomers

To a solution of 17.05g (0.07 mole) of 4-chlorophenoxyacetaldehyde in 100 ml of ether was added 9.0g (0.1 mole) of lactic acid dissolved in 50 ml of tetrahydrofuran. To the clear solution was added 15 g (0.105 mole) of boron trifluoride etherate. After 24 hours at ambient temperature, the reaction mixture was washed with aqueous sodium bicarbonate, dried, concentrated, and purified by silica chromatography. The first fraction that emerged from the column was 2-(4-chlorophenoxymethyl0-5-methyl-1,3-dioxolan-4-one, the transisomer, having a melting point of 37–40°. The second fraction was the cis isomer which melted at 53°–55°.

EXAMPLE 2

2-(2,4-Dichlorophenoxymethyl)-5-phenyl-1,3-dioxlolan-4-one, cis and trans isomers A solution containing 5.1g (0.025 mole) of 2,4-dichlorophenoxyacetaldehyde, 4.25g (0.028 mole) of mandelic acid, and 10.0g (0.07 mole) of boron trifluoride etherate in 250 ml of ether was allowed to stir for 2 hours at ambient temperature, washed with aqueous sodium carbonate and water, dried and concentrated. The residual solid was purified by silica chromatography to give 2.7g of 2-(2,4-dichloro-phenoxymethyl)-5- phenyl-1,3-dioxolan-4-one, trans isomer, having a melting point of 68°–71°.

The second fraction was 4.4g of the cis isomer melting at 105°–107°.

EXAMPLE 3

2-(4-Chloro-2-methylphenoxymethyl)-1,3-dioxolan-4-one

A solution containing 2.5g (0.033 mole) of glycolic acid, 4.1g (0.025 mole) of 4-chloro-2-methylphenoxyacetaldehdye and 10g (0.07 mole) of boron trifluoride etherate in 50 ml of ether and 30 ml of tetrahydrofuran was allowed to stand at room temperature for 24 hours. The dark solution was washed with aqueous sodium bicarbonate, dried and concentrated to dryness. Recrystallization from ether - hexane gave 3.8g of 2-(4-chloro-2-methylphenoxymethyl)-1,3-dioxolan-4-one having a melting point of 42°–44°.

EXAMPLE 4

2-(2,4-Dichlorophenoxymethyl)-1,3-oxathiolan-5-one

A solution containing 10.25g (0.05 mole) of 2,4-dichlorophenoxyacetaldehyde, 5.1g (0.055 mole) of thioglycolic acid and 15g (0.15 mole) of boron trifluoride etherate in 250 ml of ether was stirred at ambient temperature for 2 hours, washed with 5% aqueous sodium carbonate, dried, concentrated, and triturated with hexane to give 5.6g of 2-(2,4-dichlorophenoxymethyl)-1,3-oxathiolan-5-one as an off-white crystalline solid melting at 50°–61°.

EXAMPLE 5

2-(4-Chlorophenoxymethyl)-5-methyl-4-oxazolidinone, cis and trans isomers 16.9 g (0.19 mole) of lactamide was added to a solution containing 32.3 g (0.19 mole) of (4-chlorophenoxy)acetaldehyde and 0.2 g of p-toluenesulfonic acid in 500 ml of toluene. The mixture was refluxed with stirring for 5 hours while water was removed azetropically. Toluene was removed under reduced pressure and the residue, which contained at least two major compounds, was purified by silica chromatography to give 1.1 g of 2-(4-chlorophenoxymethyl)-5-methyl-4-oxazolidinone, cis isomer, as a white crystalline solid melting at 84°–86°.

A solution containing 8.5 g (0.05 mole) of 4-chlorophenoxy)acetaldehyde, 5.0 g (0.055 mole) of lactamide and 14.2 g (0.1 mole) of boron trifluoride etherate in 250 ml of anhydrous ether was allowed to stir at ambient temperature for 2 hours, washed with 5% sodium carbonate and water, dried (MgSO₄), and evaporated. Separation by silica chromatography of the residual solid gave 0.6 g of 2-(4-chlorophenoxymethyl)-5-methyl-4-oxazolidinone, trans isomer, as a white crystalline solid melting at 134°–137°.

EXAMPLE 6

2-(4-Chloro-2-methylphenoxymethyl)-4-oxazolidinone

A solution containing 4.6 g (0.025 mole) of (4-chloro-2-methylphenoxy)acetaldehyde and 2.1 g (0.028 mole) of glycolamide in 25 ml of tetrahydrofuran and 25 ml of ether was allowed to stand at ambient temperature for 24 hours. The resulting product was washed with 5% sodium carbonate and water, dried and purified by silica chromatography to give 1.1 g of 2-(4-chloro-2-methylphenoxymethyl)-4-oxazolidinone as a white crystalline solid melting at 109°–112°.

EXAMPLE 7

2-(4-Chloro-2-methylphenoxymethyl)-3-methyl-4-oxazolidinone 4.6 g (0.0325 mole) of boron trifluoride etherate was added to a solution containing 4.6 g (0.025 mole) of (4-chloro-2-methylphenoxy)acetaldehyde and 2.5 g (0.028 mole) of N-methylglycolamide in 40 ml of tetrahydrofuran. After 24 hours at ambient temperature, the reaction mixture was concentrated under reduced pressure, extracted with ether, washed with water and dried. Purification by silica chromatography gave 0.7 g of 2-(4-chloro-2-methylphenoxymethyl)-3-methyl-4-oxazolidinone as a light yellow oil.

EXAMPLE 8

2-(2,4-Dichlorophenoxymethyl)-4-thiazolidinone

To a solution containing 5.25 g (0.025 mole) of (2,4-dichlorophenoxy)acetaldehyde and 5.0 g (0.055 mole) of thioglycolamide in 100 ml of anhydrous ether was added 14.2 g (0.10 mole) of boron trifluoride etherate. The resulting solution was stirred at ambient temperature for 6 hours, washed with water, dried (MgSO₄), and concentrated to dryness. The residual solid was purified by silica chromatography to give 1.4 g of 2-(2,4-dichlorophenoxymethyl)-4-thiazolidinone as a white crystalline solid melting at 134°–136°.

EXAMPLES 9–18

Using the experimental procedures of Examples 1 through 4, additional compounds were prepared, for which physical characteristics are given in Table I.

TABLE I

| Example | Compound | Melting Point° C |
|---|---|---|
| 9 | 2-(2-methyl-4-chlorophenoxymethyl)--5-phenyl-1,3-dioxolan-4-one, | |
| | cis isomer | 71–73° |
| | trans isomer | 45–47° |
| 10 | 2-(2,4-dichlorophenoxymethyl)-5-methyl-1,3-dioxolan-4-one, | |
| | cis isomer | 57–60° |
| | trans isomer | 45–47° |
| 11 | 2-(4-chlorophenoxymethyl)-1,3-dioxolan-4-one | 50–53° |
| 12 | 2-(4-chlorophenoxymethyl)-1,3-oxathiolan-5-one | 45–48° |
| 13 | 2-(2-methyl-4-chorophenoxymethyl)-5,5-dimethyl-1,3-dioxolan-4-one | oil |
| 14 | 2-(2,4-dichlorophenoxymethyl)-1,3-dioxolan-4-one | 53–54° |
| 15 | 2-(4-chlorophenoxymethyl)-4-oxazolidinone | 118–122° |
| 16 | 2-(2,4-Dichlorophenoxymethyl)-5-methyl-4-oxazolidinone | 72–75 |
| 17 | 2-(4-Chloro-2-methylphenoxymethyl)-5-methyl-4-oxazolidinone | |
| | cis isomer | 77–82 |
| | trans isomer | 136–140 |
| 18 | 2-(4-Chloro-2-methylphenoxymethyl-3,5-dimethyl-4-oxazolidinone | |
| | cis isomer | oil |
| | trans isomer | oil |

EXAMPLE 19

HERBICIDAL ACTIVITY TESTS

The pre-emergence herbicidal activity of the heterocyclic compounds of this invention was evaluated by planting seeds of barnyard grass, garden cress, downey brome, wild mustard, green foxtail, velvet leaf, soybean, grain sorghum, cotton and wheat in test tubes, nominally measuring 25 × 200 millimeters, containing soil treated with test compound at the rate of 0.1 milligram of active compound per tube designated in Table II as Rate I or 1 milligram of active compound per tube designated in Table II as Rate II, respectively. The planted soil was held under controlled conditions of temperature, moisture, and light for 13 to 14 days. The amount of germination was then noted and the effectiveness of the test compound was rated on the basis of a 0 to 9 scale, 0 rating indicating no effect, 9 indicating death of the seedlings or no germination.

The post-emergence activity of the heterocyclic compounds of this invention was evaluated by spraying 7-day old crabgrass plants, 10-day old pigweed plants, 7-day old downey brome plants, 10-day old wild mustard, 10-day old green foxtail, 10-day old velvet leaf, 14-day old soybean plants, 14-day old grain sorghum, 14-day old cotton plants and 7-day old wheat to runoff with a liquid formulation of the test compound at the rates of 0.40 milliliters of an 0.05% solution designated Rate I in Table II, 0.40 0.56 millileters of an 0.5% solution designated Rate II in Table II. The sprayed plants were held under controlled conditions for 10 to 11 days and the effect of the test compound was then evaluated visually, the results being rated on the 0 to 9 scale described above.

The results of the pre- and post-emergence tests are summarized in Table II.

RATE EVALUATION TESTS

The herbicidal activity of the compounds of this invention was further determined with respect to several common species of weeds, by spraying a formulation of the test compound on to the soil in which the weed seeds had been planted (pre-emergence test). In each series of tests the soil was held in containers that isolated that soil into a narrow band, or row. The solution of test compound was sprayed over the band, from one end to the other, the concentration of the test compound in the formulation varying logarithmically from a higher value at one end of the band to a lower value at the other end of the band. The effect of the test compound was evaluated visually and reported as the nominal rate of application, in pounds of test compound per acre of the soil band, at which 90% inhibition of the growth of the weeds occurred, this being referred to as the 90% growth inhibition, or $GI_{90}$, dosage. Results of the tests as well as the species tested are set out in Table III.

TABLE II

RESULTS OF THE HERBICIDE ACTIVITY SCREEN

| Example | isomer | PRE-EMERGENCE SOIL | | | | | | | | | | | POST-EMERGENCE FOLIAR | | | | | | | | |
|---|---|---|---|---|---|---|---|---|---|---|---|---|---|---|---|---|---|---|---|---|
| | | Barnyard Grass | Garden Grass | Downey Brome | Wild Mustard | Green Foxtail | Velvet Leaf | Soybean | Grain Sorghum | Cotton | Wheat | Crabgrass | Pigweed | Downey Brome | Wild Mustard | Green Foxtail | Velvet Leaf | Soybean | Grain Sorghum | Cotton | Wheat |
| | | I II | I II | I II | I II | I II | I II | I II | I II | I II | I II | I II | I II | I II | I II | I II | I II | I II | I II | I II | I II |
| 1 | cis | 7 8 | 9 9 | 8 8 | 9 9 | 8 8 | 8 8 | 8 8 | 9 9 | 8 8 | 8 8 | 2 2 | 2 7 | 0 0 | 7 7 | 0 3 | 2 7 | 6 6 | 4 4 | 5 5 | 4 4 |
| 1 | trans | 8 8 | 9 9 | 9 9 | 9 9 | 8 8 | 8 8 | 8 8 | 9 9 | 8 8 | 9 9 | 0 2 | 2 7 | 0 3 | 5 8 | 0 2 | 2 7 | 7 7 | 6 6 | 7 7 | 4 4 |
| 9 | cis | 7 9 | 9 9 | 8 8 | 9 9 | 7 8 | 9 9 | 8 8 | 8 8 | 8 8 | 8 8 | 0 2 | 2 5 | 0 0 | 5 8 | 0 1 | 4 4 | 3 3 | 2 2 | 7 7 | 0 0 |
| 9 | trans | 7 8 | 8 9 | 7 8 | 9 9 | 7 7 | 8 8 | 8 8 | 8 8 | 9 9 | 8 8 | 0 0 | 2 5 | 0 0 | 5 5 | 5 6 | 1 5 | 6 6 | 0 2 | 7 7 | 0 0 |
| 10 | cis | 8 8 | 9 9 | 8 8 | 9 9 | 8 8 | 8 9 | 8 8 | 8 8 | 9 9 | 8 8 | 0 2 | 0 7 | 0 2 | 8 8 | 0 4 | 6 8 | 4 4 | 7 7 | 8 8 | 2 2 |
| 10 | trans | 7 8 | 9 9 | 8 8 | 9 9 | 7 8 | 8 9 | 8 8 | 8 8 | 8 8 | 9 9 | 0 2 | 2 9 | 2 4/7 | 8 8/0 | 4/6 1 | 9 9 | 6 6 | 6 6 | 7 7 | 3 3 |
| 2 2 | cis trans | | | | | | | | | | | | | | | | | | | + | |
| 11 | | 8 8 | 9 9 | 8 8 | 8 8 | 8 8 | 9 9 | 8 8 | 9 9 | 8 8 | 8 8 | 0 0 | 0 4 | 0 1 | 7 8 | 1 5 | 0 7 | 7 7 | 4 4 | 3 3 | 4 4 |
| 12 | | 7 7 | 9 9 | 6 9 | 9 9 | 8 8 | 9 9 | 9 9 | 8 8 | 8 8 | 0 0 | 0 0 | 3 5 | 0 8 | 7 2 | 1 7 | 3 6 | 0 0 | 3 3 | 7 7 | 0 0 |
| 3 | 9 | 8 8 | 8 8 | 8 8 | 8 8 | 7 7 | 8 9 | 9 9 | 9 9 | 9 — | 8 — | 0 8 | 2 7 | 0 4 | 6 2 | 0 3 4/2 | 3 7/7 | 6 — | 3 — | 7 — | 0 — |
| 13 | | 8 8 | 9 9 | 7 8 | 9 9 | 7 8 | 9 — | 9 — | 9 — | 9 — | 8 0/— | 0 0 | 2 7 | 0 0 | 7 8 | 3 4 | 5 — | 6 — | 3 — | 7 — | 0 — |
| 14 | | 8 8 | 9 9 | 8 9 | 9 9 | 8 8 | 9 9 | 9 9 | 9 9 | 9 9 | 8 8 | 0 2 | 0 7 | 0 2 | 7 8 | 0 1 | 3 7 | 7 7 | 4 4 | 7 7 | 0 2 |
| 4 | | 8 8 | 9 9 | 9 9 | 9 9 | 8 8 | 9 9 | 8 8 | 8 8 | 8 8 | 8 8 | 0 1 | 3 7 | 0 5 | 7 8 | 0 0 | 5 7 | 7 7 | 7 7 | 7 7 | 0 0 |
| 15 | | 6 7 | 7 7 | 2 3 | 9 9 | 2 — | 8 8 | 7 7 | 8 8 | 7 7 | 7 7 | 0 0 | 3 — | 2 — | 2 7/7 | 7 6/0 | 7 5/8 | 6 7 | 6 7 | 0 0 | 0 0 |
| 5 | cis | — 0/5 | 8/7 9 | 3 5 | 9 8/8 | — 0/8 | 8 8/9 | — 7 | — 8 | — 7 | — 9 | — 6/3/0 | 5 0/7/2 | 7 5/6/4 | — 7/7/7 | — 0/1 | — 5/5/8 | — 6 | — 4 | — 7 | — 0 |
| 5 | trans | 0 9 | 8 9 | 7 7 | 9 9 | 4 7 | 9 8 | 7 9 | 9 9 | 8 7 | 8 7 | 0 0 | 0 5 | 0 0 | — — | 0 4 | 5 7 | 6 6 | 4 4 | 3 3 | 0 0 |
| 6 | | 0 8 | 9 9 | 6 7 | 9 9 | 6 8 | 8 8 | 8 8 | 9 9 | 6 8 | 7 8 | 0 0 | 5 5 | 2 2 | — — | 0 4 | 3 5 | 6 6 | 0 0 | 7 7 | 0 0 |
| 7 | | 8 9 | 8 9 | 8 8 | 8 8 | 6 8 | 8 8 | 8 8 | 9 9 | 8 8 | 8 8 | 0 1 | 6 6 | 0 3 | — — | 5 5 | 2 8 | 5 5 | 5 5 | 7 7 | 0 0 |
| 17 | cis | 4 7 | 8 9 | 4 4 | 8 8 | 6 6 | 8 9 | 8 8 | 6 6 | 6 8 | 6 3 | 0 0 | 8 8 | 0 2 | — — | 0 2 | 2 7 | 6 6 | 2 2 | 7 7 | 3 3 |
| 17 | trans | 4 7 | 8 9 | 4 7 | 9 9 | 1 4 | 7 9 | 8 8 | 6 6 | 8 8 | 8 8 | 0 0 | 6 7 | 0 3 | — — | 0 3 | 4 8 | 5 5 | 1 1 | 3 3 | 2 2 |
| 18 | cis | 6 9 | 8 8 | 6 0 | 9 9 | 4 0 | 9 3 | 8 8 | 8 9 | 8 8 | 8 8 | 0 1 | 7 8 | 0 0 | — — | 0 3 | 6 8 | 6 6 | 3 3 | 6 6 | 2 2 |
| 18 | trans | 5 8 | 8 9 | 0 3 | 9 9 | 0 7 | 3 8 | 8 8 | 9 9 | 8 8 | 9 9 | 0 1 | 5 7 | 0 0 | — — | 0 4 | 1 6 | 5 5 | 3 3 | 6 6 | 1 1 |
| 8 | | — — | — 8 | — 7 | — 9 | — — | — 9 | — 6 | — 7 | — 8 | — 1 | — 1 | — 7 | — 1 | — — | — — | — 6 | — 4 | — 2 | — 4 | — 1 |

TABLE III

RESULTS OF THE PREEMERGENCE HERBICIDE RATE EVALUATION SCREEN- Lb/A for GI-90

| EXAMPLE | SOIL | GRASSES | | | | | BROADLEAVES | | |
|---|---|---|---|---|---|---|---|---|---|
| | | Barn-yard Grass | Crab-grass | Dow-ney Brome | Fall Pan-icum | Yel-low Foxtail | Pig-weed | Vel-vet leaf | Wild Mus-tard |
| 1 (cis isomer) | Webster soil | > 2.0 | > 2.0 | > 2.0 | 2.0 | >2.0 | 1.34 | > 2.0 | 1.5 |
| | Hanford soil | > 1.0 | > 1.0 | > 1.0 | > 1.0 | > 1.0 | 0.22 | > 1.0 | < 0.22 |
| 1 (trans isomer) | Webster soil | > 2.0 | > 2.0 | > 2.0 | < 1.0 | > 2.0 | > 2.0 | 1.36 | 1.5 |
| | Hanford soil | > 1.0 | > 1.0 | > 1.0 | 0.4 | >1 1.0 | 0.52 | 0.84 | 0.4 |
| 9 (cis isomer) | Webster soil | 1.8 | < 1.0 | > 2.0 | < 1.0 | 1.0 | < 1.0 | < 1.0 | < 1.0 |
| | Hanford soil | > 1.0 | > 1.0 | > 1.0 | 0.4 | >1 1.0 | 0.58 | 0.48 | 0.22 |
| 10 (cis isomer) | Webster soil | > 2.0 | 1.36 | > 2.0 | < 1.0 | > 2.0 | 2.0 | 1.0 | < 1.0 |
| | Hanford soil | > 2.0 | > 1.0 | > 1.0 | 0.24 | >1 1.0 | 0.52 | 0.48 | < 0.22 |
| 10 (trans isomer) | Webster soil | > 2.0 | 1.64 | > 2.0 | < 1.0 | > 2.0 | 1.36 | 1.0 | < 1.0 |
| | Hanford soil | > 1.0 | > 1.0 | 0.92 | 0.22 | > 1.0 | 0.52 | 0.48 | < 0.22 |
| 2 (cis isomer) | Webster soil | > 2.0 | > 2.0 | > 2.0 | 1.36 | > 2.0 | 1.12 | 2.0 | < 1.0 |
| | Hanford soil | > 1.0 | > 1.0 | > 1.0 | 0.22 | > 1.0 | 0.58 | > 1.0 | < 0.22 |
| 2 (trans isomer) | Webster soil | > 2.0 | > 2.0 | > 2.0 | < 1.0 | > 2.0 | 1.36 | > 2.0 | < 1.0 |
| | Hanford soil | > 1.0 | > 1.0 | > 1.0 | < 0.22 | > 1.0 | 0.22 | > 1.0 | < 0.22 |
| | Webster soil | > 2.0 | > 2.0 | > 2.0 | 1.0 | > 2.0 | 1.5 | > 2.0 | 1.5 |
| | Hanford soil | > 1.0 | > 1.0 | > 1.0 | 0.76 | > 1.0 | > 1.0 | > 1.0 | 0.48 |
| 5 (cis isomer) | Webster soil | > 5.0 | > 5.0 | > 5.0 | | | < 2.8 | | < 2.8 |
| | Hanford soil | > 2.8 | 1.9 | 2.8 | | | 21 0.55 | | 0.7 |
| 5 (trans isomer) | Webster soil | > 2.0 | > 2.0 | > 2.0 | 1.34 | > 2.0 | 1.5 | > 2.0 | 1.0 |
| | Hanford soil | > 1.0 | > 1.0 | > 1.0 | 1.0 | > 1.0 | 0.7 | > 1.0 | 0.52 |
| 6 | Webster soil | 1.36 | 2.0 | > 2.0 | 1.12 | > 2.0 | 1.0 | > 2.0 | 1.0 |
| | Hanford soil | > 1.0 | > 1.0 | > 1.0 | > 1.0 | > 1.0 | 0.76 | > 1.0 | 0.4 |
| 17 (cis isomer) | Webster soil | > 2.0 | > 2.0 | > 2.0 | 1.0 | > 2.0 | 1.0 | > 2.0 | 1.64 |
| | Hanford soil | > 1.0 | > 1.0 | > 1.0 | 0.58 | > 1.0 | > 1.0 | > 1.0 | 0.7 |
| 17 (trans isomer) | Webster soil | > 2.0 | > 2.0 | > 2.0 | > 2.0 | > 2.0 | < 1.0 | > 2.0 | 1.64 |
| | Hanford soil | > 1.0 | > 1.0 | > 1.0 | > 1.0 | 0.92 | > 1.0 | 0.84 | |
| 18 (cis isomer) | Webster soil | 1.5 | > 2.0 | > 2.0 | 1.36 | > 2.0 | 1.36 | > 2.0 | 1.64 |
| | Hanford soil | > 1.0 | > 1.0 | > 1.0 | 0.52 | > 1.0 | 0.7 | > 1.0 | 0.52 |
| 18 (trans isomer) | Webster soil | > 2.0 | > 2.0 | > 2.0 | > 2.0 | > 2.0 | < 1.0 | > 2.0 | > 2.0 |
| | Hanford soil | > 1.0 | > 1.0 | > 1.0 | > 1.0 | > 1.0 | 0.52 | > 1.0 | > 1.0 |
| 11 | Webster soil | > 2.0 | 2.0 | > 2.0 | < 1.0 | > 2.0 | > 1.0 | | |
| | Hanford soil | > 1.0 | > 1.0 | > 1.0 | 0.22 | > 1.0 | 0.64 | 0.4 | 0.22 |
| 12 | Webster soil | > 2.0 | > 2.0 | > 2.0 | < 1.0 | > 2.0 | 2.0 | > 2.0 | 1.0 |
| | Hanford soil | > 1.0 | > 1.0 | > 1.0 | < 0.22 | > 1.0 | 0.64 | 0.7 | 0.52 |
| 3 | Webster soil | 1.36 | < 1.0 | > 2.0 | < 1.0 | > 2.0 | < 1.0 | 2.0 | < 1.0 |
| | Hanford soil | > 1.0 | > 1.0 | > 1.0 | 0.4 | > 1.0 | 0.4 | 0.32 | < 0.22 |
| 13 | Webster soil | 1.36 | 1.36 | > 2.0 | < 1.0 | 1.0 | < 1.0 | < 1.0 | < 1.0 |
| | Hanford soil | > 1.0 | > 1.0 | > 1.0 | 0.22 | > 1.0 | 0.58 | 0.32 | < 0.22 |
| 14 | Webster soil | 2.0 | > 2.0 | > 2.0 | < 1.0 | > 2.0 | 1.34 | < 1.0 | < 6.0 |
| | Hanford soil | 1.0 | > 1.0 | > 1.0 | < 0.22 | 0.3 | 0.3 | 0.4 | < 0.22 |
| | Webster soil | > 2.0 | 2.0 | 1.5 | < 1.0 | > 2.0 | 1.12 | 2.0 | 1.0 |
| 4 | Hanford soil | > 1.0 | 1.0 | > 1.0 | 0.24 | > 1.0 | 0.76 | > 1.0 | 0.22 |

The symbol > means "greater than"
The symbol < means "less than"

What is claimed is:

1. A compound of the formula

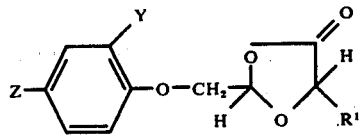

wherein Y is halogen or alkyl of 1 to 6 carbon atoms; Z is halogen and $R^1$ is hydrogen or alkyl of 1 to 6 carbon atoms.

2. A compound as claimed in claim 1 wherein Y and Z each is halogen and $R^1$ is hydrogen.

3. A compound as claimed in claim 1 wherein Y is chlorine or methyl; Z is chlorine and $R^1$ is hydrogen or methyl.

4. A compound as claimed in claim 2 wherein Y and Z each is chlorine.

5. A compound as claimed in claim 1 wherein Y and R¹ each is hydrogen and Z is chlorine.

6. A compound as claimed in claim 1 wherein Y and Z each is chlorine and R¹ is methyl.

7. A compound of the formula

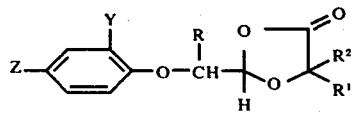

wherein Y and Z each is chlorine, R¹ is phenyl and R and R² each is hydrogen.

8. A method for controlling undesirable plant growth which comprises applying to the locus to be protected a herbicidally effective amount of a compound as claimed in claim 1 or a composition thereof.

9. A herbicidal composition comprises a compound as claimed in claim 1 and at least one surface active agent or carrier therefor.

* * * * *